US006740794B1

(12) United States Patent
Malecha et al.

(10) Patent No.: US 6,740,794 B1
(45) Date of Patent: May 25, 2004

(54) METHODS OF ISOLATING THE ANDROGENIC SEX HORMONE FROM CRUSTACEAN PRAWN AND MARINE SHRIMP AND METHODS OF USE

(75) Inventors: Spencer R. Malecha, Honolulu, HI (US); Piera S. Sun, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/494,149

(22) Filed: Jan. 28, 2000

Related U.S. Application Data

(60) Provisional application No. 60/117,716, filed on Jan. 28, 1999.

(51) Int. Cl.$^7$ .................. C12N 15/00; A01K 67/00; A01K 67/033; A61K 39/00; A61K 38/24

(52) U.S. Cl. .................. 800/22; 800/8; 424/198.1; 530/399

(58) Field of Search .................. 800/22, 8; 424/198.1; 530/399

(56) References Cited

U.S. PATENT DOCUMENTS 5,314,882 A    5/1994  Pantic et al.

FOREIGN PATENT DOCUMENTS

EP           0 514 015        11/1992

OTHER PUBLICATIONS

Nakashima; Reproductive Stratigies in a Partially Protandrous Shrimp, *Athanas kominatoensis* (Decapoda: Alpheidae): Sex Change as the Best of a Bad Situation for Subordinates, 1987, J. Ethol. 5: 145–159.*

Martin et al. "Purification and characterization of Androgenic Hormone from the Terrestrial Isopod *Armadillidium vulgare* Latr. (Crustacea, Oniscidea)," Gen Comp. Endocrinol. 80(3):349–354 (1990).

Mohamed et al. "Effect of androgenic gland ablation on sexual characters of the male Indian whit prawn *Penaeus indicus* H. Milne Edwards," Indian J. Exp. Biol. 29(5): 478–480 (1991).

Nagamine et al. "Effects of androgenic gland ablation on the male sexual characteristics in the freshwater prawn," Am. Zool 17(4):968 (1977).

Nagamine et al. "Effects of androgenic gland ablation on male primary and secondary sexual characteristics in the Malaysian Prawn, *Macrobrachium rosenbergiii* (de Man) (Decapods, Palaemonidae), with First Evidence of Induced Feminization in a Nonhermaphroditic Decapod," Gen. Comp. Endocrinol 41(4) 423–441 (1980).

Nagamine. Annual Meeting of the American Society of Zoologists, Society of Systematic Zoology and the American Microscopical Society, Tampa, Fla., Dec. 27–30, "Cloning and expression of seminal vesicle specific peptide of terrestrial isopod, *Armadillidium vulgare*," Endocrinology, 8: abstract.

Negishi et al. "Alterations in the integument of *Armadillidium vulgare* masculinized by implantation of androgenic glands," Invertebrate Reproduction and Development, 21(3):179–186 (1992).

Negishi et al. Sixty–Second Annual Meeting of the Zoological Society of Japan, Oct. 13–15 (1991). Endocrinology, 1183: abstract.

Okuno et al. "Characterization and cDNA cloning of androgenic gland hormone of the terrestrial isopod *Armadillidium vulgare*," Biochem. Biophys. Res. Commun. 264(2):419–423 (1999).

Okuno et al. "Purification and properties of androgenic gland hormone from the terrestrial isopod *Armadillidium vulgare*," Zoological Science (Tokyo) 14(5):837–842 (1997).

Okuno et al. "Purification and properties of the androgenic gland hormone from the terrestrial isopod," Endocrinology, 7, abstract.

Payen et al. 11th conference European Comparative Endocrinologists, Jerusalem, Israel, Aug. 10–14 (1981). Gen Comp Endocrinol 46(3) (1982).

Payen. C R Hebd Seances Acad Sci Ser D Sci Nat. 280(9):1111–1114 (1975).

Raimond et al. General and Comparative Endocrinology, 50(1): 146–155 (1983), English abstract.

Sagi et al. Revista da Sociedade Brasileira de Zootecnia, 24(2):300–309 (1995), English abstract.

Sagi et al. "Intersex Red Claw Crayfish, *Cherax quadricarinatus* (von Martens): Functional males with pre–vitellogenic ovaries,"Biological Bulletin. 190(1): 16–23 (1996).

Sagi et al. "Effect of androgenic gland ablation on morphotypic differentiation and sexual characteristics of male freshwater prawns, *Macrobrachium rosenbergii*," Gen Comp Endocrinol 77(1):15–22 (1990).

(List continued on next page.)

*Primary Examiner*—Peter Paras
(74) *Attorney, Agent, or Firm*—Dorsey & Whitney; Richard F. Trecartin; Traci H. Ropp

(57) ABSTRACT

This work constitutes a novel approach and methodology, e.g., the in vitro secretion method to isolate the androgenic polypeptide hormone (AH) from the androgenic gland of shrimp or prawns. Alternatively, the AH can be obtained recombinantly by cloning and expressing the AH gene. The AH polypeptide is used to produce phenotypic males, neomales, from genotypic female shrimp or prawns. The neomales find use in the production of sex-skewed and monosex offspring when mated with wild-type female shrimp or prawns. From the sequence of the purified AH polypeptide, oligonucleotide probes are synthesized to clone the AH encoding nucleic acid which is used for recombinant AH polypeptide expression.

4 Claims, 3 Drawing Sheets

OTHER PUBLICATIONS

Nagamine et al., "Masculinization of Female *Macrobrachium rosenbergil* (de Man) (Decapoda, Palaemonidae) by Androgenic Gland Implantation," General and Comparative Endocrinology, 41:442–457 (1980).

Malecha et al., "Sex Ratios and Sex–determination in progeny from crosses of surgically sex–reversed freshwater prawns, *Macrobrachium rosenbergii*," Aquaculture, 105:201–218 (1992).

Bonilla et al., Rev. Biol. Trop 42(suppl. 2):121–129 (1994), English abstract.

Chang et al., "Prostatic Spemine–binding Protein," J. Biol. Chem. 262(6):2826–2831 (1987).

Fowler et al. "The structure and function of the androgenic gland in Cherax destructor (Decapoda: Parastacidae," Aquaculture, 171(1–2):135–148 (1999).

Hasegawa et al. "Masculinization of Female by the newly-formed Androgenic Glands in the ZW and WW females of the Isopod Crustacean," Zool Sci (Tokyo), 2(3):419–422 (1985).

Hasegawa et al. "Isolation and Properties of Androgenic Gland Hormone from the Terrestrial Isopod, *Armadillidium vulgare*," Gen. Comp. Endocrinol. 67(1):101–110 (1987).

Hasegawa et al. "Masculinization of WW females in the Isopod Crustacean, *Armadillidium vulgare*," Annot Zool Jpn. 56(3):163–166 (1984).

Juchault et al. General and Comparative Endocrinology, 36(2):175–186 (1978), English abstract.

Katakura et al. "Purification of androgenic gland hormone from the terrestrial isopod, *Armadillidium vulgare* (Latreille, 1804)," Monitore Zoologico Italiano (Italian Journal of Zoology No. 4) 351–358 (1989).

Katakura et al. "Masculinization of females of the Isopod Curstacean, *Armadillidium vulgare*, following injections of an active extract of the Androgenic Gland," Gen Comp. Endocrinol. 48: 57–62 (1983).

Katakura et al. "Isolation of androgenic gland hormone by high performance liquid chromatography," Endocrinology, P. 962, EN11. 55th Annual Meeting of the Zoological Society of Japan, Morioka. Sep. 27–29 1984. Zool Sci. (Tokyo) 1(6) 1984.

Legrand–Hamelin. C R Seances Soc Biol Fil 171(1):176–180 (1977), English abstract.

Martin et al. "The structure of a glycosylated protein hormone responsible for sex determination in the isopod, *Armadillidium vulgare*," Eur. J. Biochem. 262(3):727–736 (1999).

Sagi et al. American Zoologist, 36(5):10a (1996).

Sagi et al. "Sexual differentiation in decapod crustaceans: role of the androgenic gland," Invertebrate Reproduction and Development. 31(1–3):55–61 (1997).

Sagi et al. American Zoologist 37(5):183a (1997).

Suzuki, S. "Sex–Reversal of male *Armadillidium vulgare* (Isopods, Malacostraca, Crustacea) following andrectomy and partial Gonadectomy," Gen Comp Endocrinol. 83(3):375–378 (1991).

Suzuki, S. "Sexual bipotentiality of developing ovaries in the terrestrial isopod *Armadillidium vulgare* (Malacostraca, Crustacea)," Gen Comp Endocrinol. 107(1):136–146 (1997).

Suzuki, S. "Sex reversal by implantation of ethanol–treated androgenic glands of female isopods, *Armadillidium vulgare* (Malacostraca, Crustacea)," Gen Comp Endocrinol. 111(3):367–375 (1998).

Suzuki, S. "Androgenic gland hormone is a sex–reversing factor but cannot be a sex–determining factor in the female Crustacean Isopods *Armadillidium vulgare*," Gen Comp Endocrinol. 115(3):370–378 (1999).

Suzuki, S. Zoological Science (Tokyo) 13(supp.) 7 (1996).

Taketomi et al. "Implantation of androgenic glands into immature female crayfish, procambarus clarkii, with Masculinization of sexual characteristics," Journal of Crustacean Biology, 16(2):232–239 (1996).

Thampy et al. "Sex–reversal and androgenic gland in the fish parasite irona far (Cymothoidae: Isopoda: Crustacea)," Int J. Parasitol 4(6): 575–584 (1974 or 1975).

\* cited by examiner

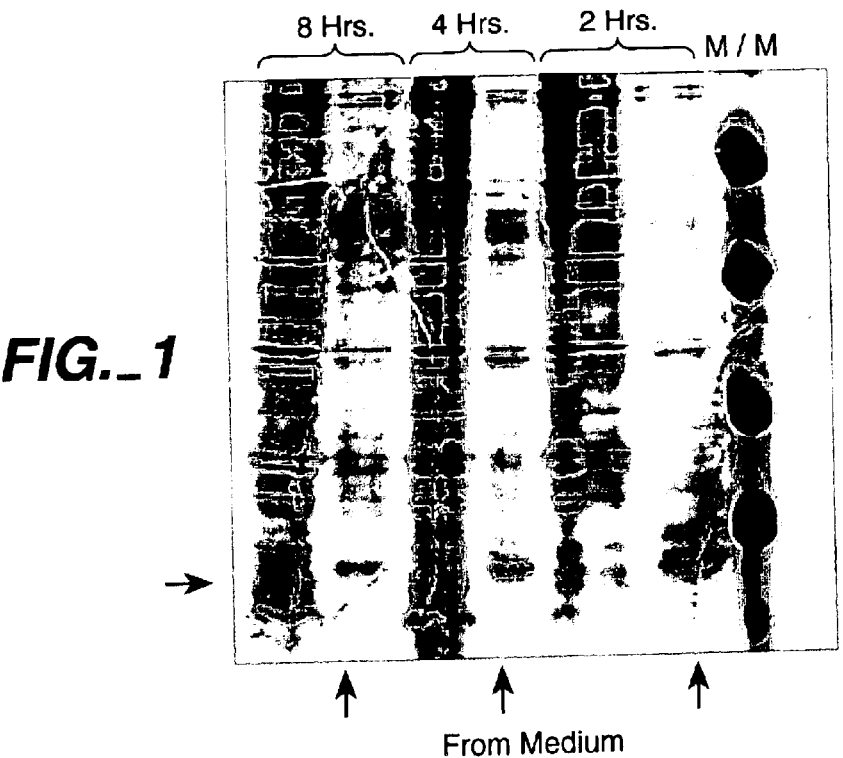
FIG._1
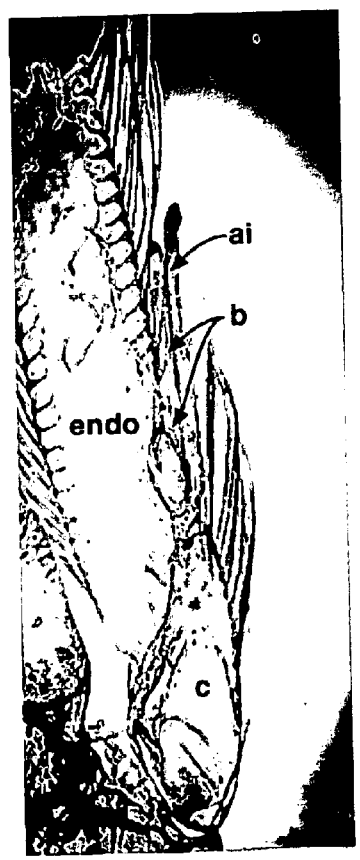
FIG._2

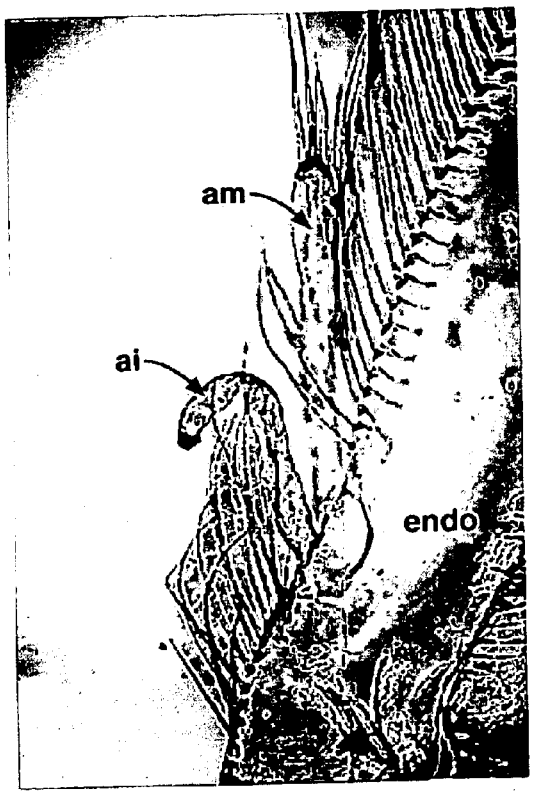
FIG._3
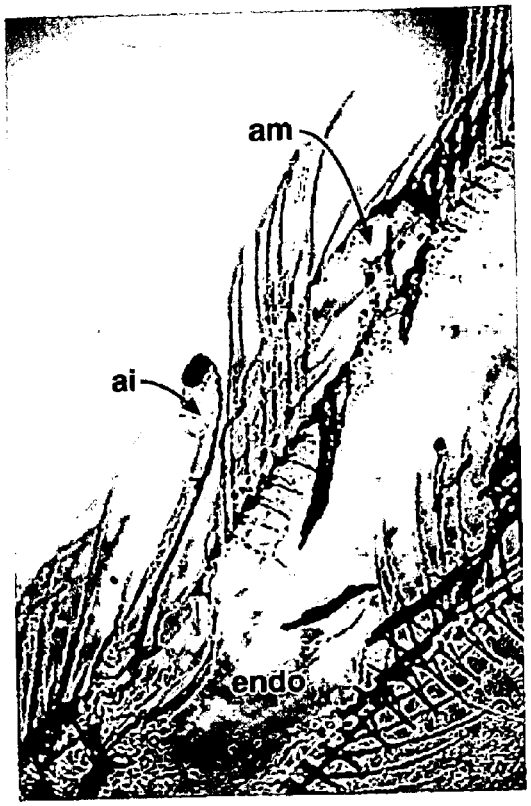
FIG._4

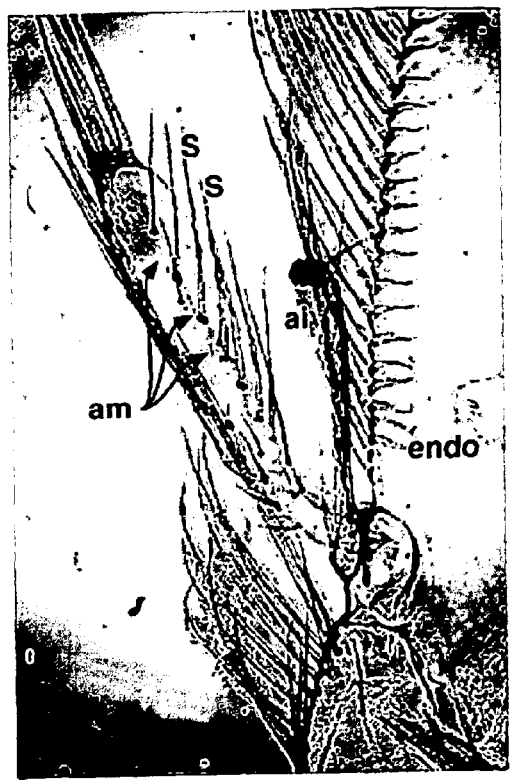
FIG._5
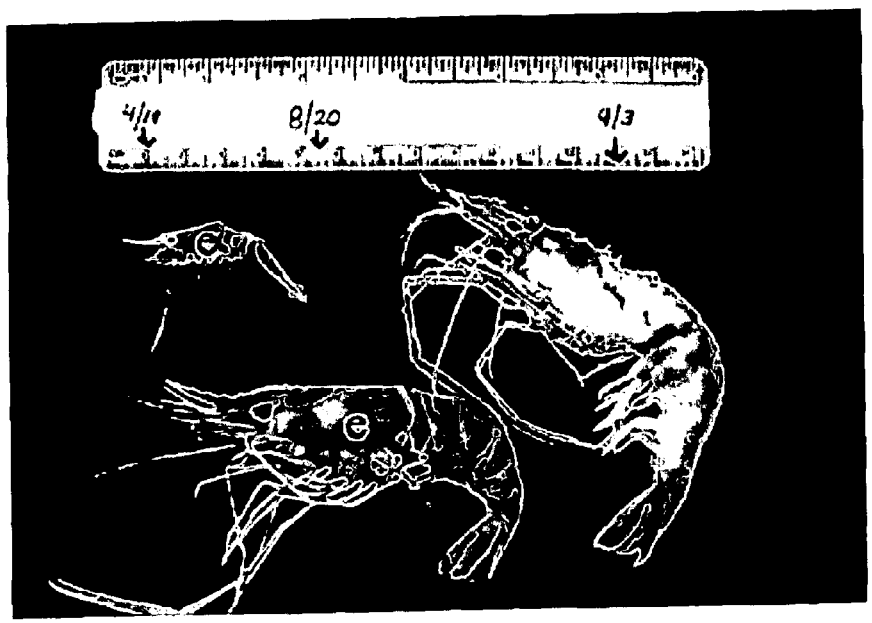
FIG._6

METHODS OF ISOLATING THE ANDROGENIC SEX HORMONE FROM CRUSTACEAN PRAWN AND MARINE SHRIMP AND METHODS OF USE

This application is a Provisional of U.S. Application Serial No. 60/117,716 filed Jan. 28, 1999, pending.

FIELD OF THE INVENTION

A technique for in vitro secretion of androgenic sex hormone (AH) from the androgenic gland (AG) of fresh water male prawn in a defined culture medium is disclosed. AH finds use in the manipulation of the reproductive processes of prawns and shrimp for the production of sex-skewed or mono-sex progeny.

BACKGROUND OF THE INVENTION

Sexual differentiation and gametogenesis in the decapods, marine shrimp (genus Penaeus) and freshwater prawns (genus Macrobrachium), occurs, respectively, in the anatomically separate testes and Androgenic Hormone (AH)-producing Androgenic Gland (AG).

Nagamine et al. (1980b) Gen. Comp. Endocrin. 41:423–441 partially sex-reversed genetic male decapods (prawns) to phenotypic females by AG ablation. This was subsequently confirmed by Sagi and Cohen (1991). Nagamine et al. (1980a) Gen. Comp. Endocrin. 41:442–457 partially sex-reversed genetic female prawns to "neomales" by AG implantation. Malecha et al. (1992a) Aquaculture 105:1–18 extended this work to smaller female recipients and achieved sex-reversal by AG implantation such that neomales produced skewed sex ratio, predominantly female, progeny when mated with normal females.

The surgical implantation of AG tissue in genetic females to produce neomales is time consuming, tedious, and is not amenable to large-scale practices. Accordingly, it is an object of the present invention to provide isolated shrimp or prawn AH. It is also an object to provide methods for use of AH in the production of neomales from genetic females and sex-skewed or mono-sex shrimp or prawn progeny, therefrom.

SUMMARY OF THE INVENTION

In accordance with the foregoing object, the present invention provides an isolated shrimp or prawn androgenic polypeptide and methods of use.

Accordingly, the invention provides neomale shrimp and prawns which do not contain transplanted androgenic gland tissue.

In another aspect, the invention provides methods of producing neomale shrimp and prawns.

In yet another aspect, the invention provides methods of producing a population of shrimp and prawns having a skewed percentage in favor of females to males.

In a further aspect, the invention provides a method of identifying an agent that binds or modulates the biological activity of an androgenic polypeptide of shrimp or prawns. Accordingly, the invention provides agents that bind to or modulate an androgenic polypeptide of a shrimp or protein.

Other embodiments or aspects of the invention will become apparent to the skilled artisan by the following description of the invention.

BRIEF DESCRIPTION OF THE DRAWINGS

FIG. 1 shows a photograph of an SDS-polyacrylamide gel of AH secreted by AG cultured in vitro at time points 2, 4, and 8 hours. M/M=molecular weight markers. AG secreted into the culture medium are indicated by arrows. The adjacent lanes within each time point are from AG cell free homogenates.

FIG. 2 shows the second pleopod from the first molted exuvium of animal no. 6 (Table 1) Showing the appendix masculina bud ("b")on the first molted exuvium, indicated in Table 1 as the first molt 13 days after the start of the protocol. The bud is located at the base of endopod segment ("endo") at the base of the appendix interna ("ai") attached to the coxa ("c") or pleopod base which attaches to the prawn ventral tail area.

FIG. 3 shows the second pleopod on the exuvium of the third molt of animal no. 6 (Table 1) showing a whole appendix masculina ("am") with setae on its terminus. The terminus of the appendix interna ("ai") is bent due to tension placed on it during the photographing procedure. Normally the appendix interna is straight, as seen in the other figures. Both the appendix masculina and appendix interna emanate from the endopod ("endo") segment of the second pleopod.

FIG. 4 shows the second pleopod on the exuvium of the fourth molt of animal no. 6 (Table 1) showing a fully developed appendix masculina ("am") and appendix interna ("ai"). The appendix masculina is lying close to the endopod ("endo") and is not fully extended from it due to the rigid position it assumed in the alcohol preservative.

FIG. 5 shows the second pleopod of a sex-reversed neomale in the AG implantation group showing an appendix masculina-fully extended from the endopod ("endo")-approximately the same developmental stage as the appendix masculina shown in FIG. 3 with well developed setae ("s").

The appendix interna ("ai") is partially hidden by setae on the endopod.

FIG. 6 shows material from sex-reversed neomale animal no. 1 (Table 1) showing a developmental sequence of two molted exuvia ("e") and an intact animal. The intact exuvium of the first molt is the left specimen under "I" on the ruler), the intact exuvium of the seventh molt is the middle specimen under "II" on ruler, and the intact animal that sacrificed at the termination of the protocol is the right specimen under "III" on the ruler. Top ruler scale is in inches and the bottom ruler scale is in centimeters.

DESCRIPTION OF PREFERRED EMBODIMENTS

The present invention provides AH polypeptide isolated from a shrimp or prawn. Accordingly, the invention provides a method of producing an AH polypeptide from an AG in culture and methods for AH extraction and purification.

In another embodiment, the present invention provides variants of the AH polypeptide.

In an additional embodiment, the present invention provides a method for isolating a nucleic acid encoding an AH polypeptide of a shrimp or prawn and expression vectors and methods for their use in the recombinant expression of AH. The present invention therefore also provides transformed host cells comprising the expression vectors and methods for their use in AH production.

In yet another embodiment, the present invention provides AH compositions and methods for their administration to genotypic females for the production of phenotypically neomale shrimp or prawns.

In a further embodiment, the present invention provides methods of producing sex-skewed or mono-sex shrimp or prawn progeny.

"AH polypeptide", "AH protein" and "AH" when used herein encompasses native sequence AH and AH variants (which are further defined herein) of prawns or shrimp. The AH may be isolated from a variety of sources, such as from AG tissue or from another source, or prepared by recombinant and/or synthetic methods. In one embodiment, AH will have a sequence comprising the same amino acid sequence as an AH derived from nature. An AH having a sequence that occurs in nature can be isolated from nature or can be produced by recombinant and/or synthetic means. The term "native sequence AH" specifically encompasses naturally-occurring truncated or secreted forms, naturally-occurring variant forms, such as, naturally-occurring allelic variants of the AH. In a preferred embodiment of the invention, the native sequence AH is a full-length or mature native sequence AH.

In one embodiment, AH is purified or isolated from freshly dissected AG. AG is removed from shrimp or prawns and cultured in vitro. The AGs produce and secrete AH directly into the culture medium.

The AG is separated from the culture medium by, for example, centrifugation. AH is typically purified, concentrated, or analyzed directly from the culture medium by a number of methods as known in the art. In a preferred embodiment, the culture media is desalted and concentrated. In another preferred embodiment, the AH from the culture media is electrophoresed on SDS-polyacrylamide gels. AH can be analyzed, for example, by transfer from the polyacrylamide gel to an appropriate membrane and stained. Alternatively, the AH can be excised from the membrane and subjected to amino and carboxy terminal amino acid sequencing. In a preferred embodiment, the AH polypeptide is isolated by chromatography, for example, ion exchange chromatography, HPLC, molecular exclusion chromatography, affinity chromatography, etc.

By "isolated AH" herein is meant an AH polypeptide that has been separated and/or recovered from a component of its natural environment. Contaminant components of its natural environment are materials that would typically interfere with the uses for the polypeptide, and may include enzymes, hormones, and other proteinaceous or non-proteinaceous solutes. In preferred embodiments, the polypeptide will be purified for example (1) to a degree sufficient for of chemical sequencing, such as, N-terminal, internal amino acid or C-terminal sequencing, (2) to a degree sufficient for sequencing by mass spectroscopy, preferably matrix-assisted laser desorption ionization-time of flight analysis (MALDI-TOF), or (3) to homogeneity by SDS-PAGE under non-reducing or reducing conditions using Coomassie blue or, preferably, silver stain. Isolated AH polypeptide includes polypeptide in situ within recombinant cells, since at least one component of the AH natural environment will not be present. Ordinarily, however, an isolated polypeptide will be prepared by at least one purification step.

By "isolated AG" herein is meant an AG that has been separated and/or recovered from a component of its natural environment. Contaminant components of its natural environment are materials that would typically interfere with the sues of the AG, and may include enzymes, hormones, and other proteinaceous or non-proteinaceous solutes, and other tissues and cells. In a preferred embodiment, the AG will be purified or isolated by surgical removal of a shrimp or prawn.

Once produced, AH find use in a number of applications. In one embodiment, AH is used to treat genetic female shrimp or prawns via injection or in enteric coated feeds to produce neomales. Preferably, prawn AH is administered to prawns and shrimp AH is administered to shrimp. Very small amounts of the AH are required for a very short development window period. Host female shrimp or prawns are preferably identified by the presence of a female nanopore complex and/or the absence of a male appendix masculina. The age of the female shrimp or prawns is preferably from about 30 to 60 days old, more preferably from about 30 to 50 days old, and most preferably from about 30 to 40 days old. Therefore, the female shrimp or prawns are at least about 30 days old which is determined from the time they have undergone metamorphosis from the final larval stages to a post-larval (PL) or small juvenile stage. The length of the female shrimp or prawns is preferably from about 1 to 5.0 cm in length, more preferably from about 1 to 2.5 cm in length even more preferably from about 1 to 2 cm in length, and most preferably from about 1 to 1.5 cm in length. In a preferred embodiment, the AH is injected as described herein in a dose preferably from about 2 to 30 Units/dose, more preferably from about 2 to 20 Units/dose, and most preferably from about 2 to 10 Units/dose. One Unit is defined as being about the equivalent of 1 AG isolated as described herein from an animal with a mass of at least about 25 g or higher. The shrimp or prawns are preferably injected with AH on Day 0 and inspected for appendix masculina development. AH injection can be repeated, for example, each week thereafter (i.e., Day 7, 14, 21 etc.) at the discretion of the practitioner until sex-reversal or masculinization is achieved, as described below. The AH administration can be given irrespective of the animals molting.

In one embodiment, AH is used to treat genetic female shrimp or prawns by contacting or immersion of shrimp or prawns in medium containing AH; In a preferred embodiment, post larvae ("PL"), shrimp or prawns of about 0 to 60 days old are used, preferably of about 0 to 30 days old, more preferably of about 0 to 20 days old, and most preferably 0 to 15 days old, The age of PL shrimp or prawns is measured as the time in days from which they developed from the last larval stage to the PL stage. In one embodiment, isolated androgenic gland (AG) tissue of a shrimp or prawn is placed in medium water which contains PL hosts, which are examined for masculinization. The PL hosts can be repeatedly treated as needed as the discretion of the practitioner until sex-reversal or masculinization is achieved, as described below The presence of neomales determined by AH treated populations that have a male to female (M:F) ratio skewed in favor of males (for example, at least about 2:1, males to females). Alternatively, neomales are identified by breeding with genetic and phenotypic females whereby offspring that have a skewed M:F ratio in favor of males are produced.

In a preferred embodiment, AH is incorporated in feeds preferably from cell-free extracts or recombinantly expressed methods or chemically synthesized methods. In one embodiment, the AH polypeptide is incorporated into the feed. In another, AH polypeptide is microencapsulated using shell materials, such as, synthetic polymerase, natural gums, waxes, or resins, thereby allowing a desired release mechanisms, for example, mechanical rupture, thermal relase, or permeation as known in the art. The release mechanism provides controlled bioavailability (Hoch. Food Processing. April 1997:49–50). Accordingly, PL female shrimp or prawns are provided feed comprising AH polypeptide or microencapsulated AH polypeptide and are examined as described herein for the development of neomales. In a preferred embodiment, the microencapsulation prevents digestion of the AH polypeptide in the stomach and allows release of the AH polypeptide after leaving the stomach.

"Neomale" herein is meant a genotypic female shrimp or prawn that has been sex-reversed according to the methods of the invention that contains at least one male sexual characteristic, such as, the an appearance of an appendix masculina, a male gonopore complex, masculine chelipeds, initiation of spermatogenesis, or the development of sperm duct segments. In a preferred embodiment a neomale shrimp or prawn is sexually mature and produces viable offspring when bred or mated with a phenotypic and genotypic or wild-type female.

Once obtained, neomales find use in the production of sex-skewed populations of shimp or prawns. When neomales are bred or mated with genotypic females the progeny will be sex-skewed to comprise a disproportionate number of females to males in comparison to the proporsion of females to males produced by breeding normal males and females. Preferably, the progeny contain sex-skewed female-to-male ratios of greater than about 3:1; more preferably of about 10:1, and most preferably of about 20:1. In some embodiments the progeny will be about 100% female.

The regulation of sex-determination and the production of sex-skewed or mono-sex progeny on a large scale that avoids the use of transplanted AG tissue will have a significant impact on commercial marine shrimp (*P. vannamei, P. chinensis P. japonicus, P. monodon*) and freshwater prawn (*M. rosenberqii*) aquaculture production because female shrimp and prawns provide a significant economic advantage over their male counterparts. For example, female Asian tiger shrimp, *P. chinensis*, Chinese white shrimp, *P. chinensis*, nee:*P. orientalis*, reach 20–30% larger body sizes than males. The Japanese kuruma shrimp, *P. japonicus*, also displays female-superior sexual dimorphism (Nakamura, (1992) Mem. Fac. Fish. Kagoshima Univ. 41:87–94). Although it has not been reported it is believed that *P. vannamei* is also sexually dimorphic. The Chinese white shrimp also has the potential to maximize production as a second crop to *P. vannamei* in the cooler —November to April—season (Main and Fulks. (1990) Proceedings of an Asian-US Workshop on Shrimp Culture. The Oceanic Institute, Makeup Hawaii. April 1990) because it displays a female-superior cold tolerance down to 7° C., a point at which the males die (Cheng, 1984 The prawn (Penaeus) in Penaeid Shrimps-Their Biology and Management. J. A. Guilland and B. J. Rothschild (ads) Fishing New Books Ltd.; Jingyao, 1981 Studies on the growth of Penaeid shrimp (*Penaeus kishinouye*) in the Gulf of Po-Hai. Marine Fisheries Research No.2, pp 85–93; Mako et al., 1966. Bull. Seikai Reg. Fish Lab. (34):1–10; Weiquan, 1984. Ocean. Limnol. Sinica 15(3):266–273; Zhang, 1987. Mar. Sci. Bull. Haiyang Tongbao 6(2):71–76). Moreover, the ability to produce all female *P. vannamei* broods will greatly enhance the broodstock industry which features the rearing and sale of large adult females.

In an alternative embodiment, AH is produced by culturing cells transformed or transfected with a vector containing an isolated AH nucleic acid. It is, of course, contemplated that alternative methods, which are well known in the art, may be employed to prepare AH. For instance, the AH sequence, or portions thereof, may be produced by direct peptide synthesis using solid-phase techniques [see, e.g., Stewart et al., *Solid-Phase Peitide Synthesis*, W.H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturers instructions. Various portions of the AH may be chemically synthesized separately and combined using chemical or enzymatic methods to produce the fulllength AH.

An "isolated" nucleic acid molecule encoding an AH polypeptide is a nucleic acid molecule that is identified and separated from at least one contaminant nucleic acid molecule with which it is ordinarily associated in the natural source of the AH-encoding nucleic acid. An isolated AH-encoding nucleic acid molecule is other than in the form or setting in which it is found in nature. Isolated nucleic acid molecules therefore are distinguished from the AH-encoding nucleic acid molecule as it exists in natural cells. However, an isolated nucleic acid molecule encoding an AH polypeptide includes AH-encoding nucleic acid molecules contained in cells that ordinarily express AH where, for example, the nucleic acid molecule is in a chromosomal location different from that of natural cells.

DNA encoding AH may be obtained from a CDNA library prepared from AG tissue using the AG mRNA. In an alternative embodiment, substractive hybridization using mRNA from a cell or tissue that does not produce AH may be used prior to the construction of the library to bias the library to contain primarily those sequences that are expressed by AG. The AH-encoding gene may also be obtained from a genomic library. In a preferred embodiment, DNA encoding AH is obtained using methods similar to those employed by Sun (1994) *Mol. Mar. Biol. Biotechnol.* 3(1):1–6 for the shrimp molt inhibitory hormone (MIH; a hormone produced by a gland in the base of the shrimp eye stalk).

Libraries can be screened with probes (such as antibodies to the AH or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding AH is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The sequence of the oligonucleotide probe can be derived from reverse translation of at least a portion of the amino acid sequence of AH polypeptide. Due to the degeneracy of the genetic code, degenerate probes may be synthesized to contain all possible permutations of the nucleic acid sequence that may encode the AH amino acid sequence. Preferably, the nucleic acid sequence of the oligonucleotide probe is biased to contain codon sequences that are found at a higher frequency in shrimp or prawn genomes. The oligonucleotide is preferably labeled such that it can be detected upon hybridization to DNA in the library being screened. Methods of labeling are well known in the art, and include the use of radiolabels like $^{32}$P-labeled ATP, biotinylation, digoxigenin or enzyme labeling (Molecular Probes Handbook of Fluorescent Probes and Research Chemicals, 6th edt. by Richard P. Haugland). Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the fulllength sequence can be determined through sequence alignment using computer software programs such as ALIGN, DNAstar, BLAST, BLAST2 and INHERIT which employ various algorithms to measure homology.

Nucleic acid having AH polypeptide coding sequence may be obtained by screening selected cDNA or genomic libraries using the deduced amino acid sequence, and, if necessary, using conventional primer extension procedures as described in Sambrook et al., supra, to detect precursors and processing intermediates of mRNA that may not have been reverse-transcribed into cDNA.

Host cells are transfected or transformed with expression or cloning vectors described herein for AH production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach,* M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described by Shaw et al., *Gene,* 23:315 (1983) and WO 89/05859 published Jun. 29, 1989. For mammalian cells without such cell walls, the calcium phosphate precipitation method of Graham and van der Eb, *Virology,* 52:456–457 (1978) can be employed. General aspects of mammalian cell host system transformations have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA),* 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology,* 185:527–537 (1990) and Mansour et al., *Nature,* 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli.* Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for AH-encoding vectors. *Saccharomyces cerevisiae* is a commonly used lower eukaryotc host microorganism.

Suitable host cells for the expression of glycosylated AH, if desired, are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR (CHO, Urlaub and Chasin, *Proc. Natl. Acad. Sci. USA* 77:4216 (1980)); mouse sertoli cells (TM4, Mather, *Biol. Reprod.,* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

The nucleic acid (e.g., cDNA or genomic DNA) encoding AH may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The AH may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the AH-encoding DNA that is inserted into the vector. The signal sequence may be a prokaryotic signal sequence selected, for example, from the group of the alkaline phosphatase, penicillinase, or heat-stable enterotoxin II leaders. For yeast secretion the signal sequence may be, e.g., the yeast invertase leader, alpha factor leader (including Saccharomyces and Kluyveromyces alpha-factor leaders, the latter described in U.S. Pat. No. 5,010,182), or acid phosphatase leader, the C. albicans glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors will typically contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2m plasmid origin is suitable for yeast and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the AH-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene* 7:141 (1979); Tschemper et al., *Gene,* 10:157 (1980)3. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain control sequences operably linked to the AH-encoding nucleic acid sequence to direct mRNA synthesis. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence operably linked to the DNA encoding AH.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Req.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

AH transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the AH by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at apposition 5' or 3' to the AH coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding AH.

Still other methods, vectors, and host cells suitable for adaptation to the synthesis of AH in recombinant vertebrate cell culture are described in Gething et al., *Nature,* 293:620–625 (1981); Mantei et al., *Nature,* 281:40–46 (1979); EP 117,060; and EP 117,058.

Gene amplification and/or expression may be measured in a sample directly, for example, by conventional Southern blotting, Northern blotting to quantitate the transcription of mRNA [Thomas, *Proc. Natl. Acad. Sci. USA,* 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected AH expression, alternatively, may be measured by immunological methods, such as immunohistochemical staining of cells or tissue sections and assay of cell culture or body fluids, to quantitate directly the expression of AH. Antibodies useful for immunohistochemical staining and/or assay of sample fluids may be either monoclonal or polyclonal, and may be prepared in any mammal. Conveniently, the antibodies may be prepared against a native sequence AH polypeptide or against a synthetic peptide based on the encoding DNA sequences or against exogenous sequence fused to AH DNA and encoding a specific antibody epitope.

In a prefered embodiment, AH expression may be measured in a sample in terms of its biological activity, such as, in its activity in the sex-reversal of female shrimp or prawns to produce neomale shrimp or prawns, as described herein.

Forms of AH may be recovered from culture medium or from host cell lysates. If membrane-bound, AH can be released from the membrane using a suitable detergent solution (e.g. Triton-X 100) or by enzymatic cleavage. Cells employed in expression of AH can be disrupted by various physical or chemical means, such as freeze-thaw cycling, sonication, mechanical disruption, or cell lysing agents.

It may be desired to purify AH from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; desalting and centrifugal filtration, using for example a Microcon centrifugal filter device; protein A Sepharose columns to remove contaminants such as IgG; and metal chelating columns to bind epitope-tagged forms of the AH. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular AH produced.

DNA or RNA nucleotide sequences (or their complement) encoding AH have various applications in the art of molecular biology, including uses as hybridization probes, in chromosome and gene mapping and in the generation of anti-sense RNA and DNA. AH nucleic acid will also be useful for the preparation of AH polypeptides by the recombinant techniques described herein.

The full-length native sequence AH gene, or portions thereof, may be used as hybridization probes for a cDNA library to isolate the full-length AH gene or to isolate still other genes (for instance, those encoding naturally occurring variants of AH or AH from other species) which have a desired sequence identity to the AH coding sequence. Optionally, the length of the probes will be about 20 to about 50 bases. The hybridization probes may be derived from the nucleotide sequence or from genomic sequences including promoters, enhancer elements and introns of native sequence AH. By way of example, a screening method will comprise isolating the coding region of the AH gene using the known DNA sequence to synthesize a selected probe of about 40 bases. Hybridization probes may be labeled by a variety of labels, including radionucleotides such as P-32 or S-35, or enzymatic labels such as alkaline phosphatase coupled to the probe via avidin/biotin coupling systems. Labeled probes having a sequence complementary to that of the AH gene of the present invention can be used to screen libraries of human CDNA, genomic DNA or mRNA to determine which members of such libraries the probe hybridizes to.

The probes may also be employed in PCR techniques to generate a pool of sequences for identification of closely related AH coding sequences.

Nucleotide sequences encoding an AH can also be used to construct hybridization probes for mapping the gene which encodes that AH and for the genetic analysis of individuals with genetic disorders.

The nucleotide sequences provided herein may be mapped to a chromosome and specific regions of a chromosome using known techniques, such as in situ hybridization, linkage analysis against known chromosomal markers, and hybridization screening with libraries.

"Stringency" of hybridization reactions is readily determinable by one of ordinary skill in the art, and generally is an empirical calculation dependent upon probe length, washing temperature, salt concentration, and the concentration of denaturing or helix-destabilizing agents In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 mg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and %SDS) less stringent that those described above. An example of moderately stringent conditions is overnight Incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The present invention further provides AH variants. "AH variant" means an active AH as defined below having at least about 80% amino acid sequence identity with the amino acid sequence of the AH polypeptide. Such AH variants include, for instance, AH polypeptides wherein one or more amino acid residues are added, or deleted, at the N- or C-terminus, as well as within one or more internal domains. The term "AH variant" does not encompass the native AH sequence. Ordinarily, an AH variant will have at least about 80% amino acid sequence identity, more preferably at least about 85% amino acid sequence identity, even more preferably at least about 90% amino acid sequence identity, and most preferably at least about 95% sequence identity with the amino acid sequence of native AH.

By "homology" herein is meant sequence similarity and identity with identity being preferred.

By "percent (%) amino acid sequence identity" with respect to the AH sequences is defined herein as the percentage of amino acid residues in a candidate sequence that are identical with the amino acid residues in the AH sequence, after aligning the sequences and introducing gaps, if necessary, to achieve the maximum percent sequence identity, and not considering any conservative substitutions as part of the sequence identity. The % identity values used herein are generated by Wu-BLAST-2 which was obtained from Altschul et al., *Methods in Enzymology,* 266: 460–480 (1996); http://blast.wustl/edu/blas/README.html. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The term "positives", in the context of sequence comparison performed as described above, includes residues in the sequences compared that are not identical but have similar properties (e.g. as a result of conservative substitutions). The % value of positives is determined by the fraction of residues scoring a positive value in the BLOSUM 62 matrix divided by the total number of residues in the longer sequence, as defined above.

In a similar manner, "percent (%) nucleic acid sequence identity" with respect to the coding sequence of the AH polypeptides and variants identified herein is defined as the percentage of nucleotide residues in a candidate sequence that are identical with the nucleotide residues in the AH coding sequence. The identity values used herein were generated by the BLASTN module of WU-BLAST-2 set to the default parameters, with overlap span and overlap fraction set to 1 and 0.125, respectively.

AH variants can be prepared by introducing appropriate nucleotide changes into the DNA encoding AH, and/or by synthesis of the desired AH polypeptide. Those skilled in the art will appreciate that amino acid changes may alter post-translational processes of the AH, such as changing the number or position of glycosylabon sites or altering the membrane anchoring characteristics.

Variations in the native full-length sequence AH or in various domains of the AH can be made, for example, using any of the techniques and guidelines for conservative and non-conservative mutations set forth, for instance, in U.S. Pat. No. 5,364,934. Variations may be a substitution, deletion or insertion of one or more codons encoding the AH that results in a change in the amino acid sequence of the AH as compared with the native sequence AH. Optionally the variation is by substitution of at least one amino acid with any other amino acid in one or more of the domains of the AH. Guidance in determining which amino acid residue may be inserted, substituted or deleted without adversely affecting the desired activity may be found by comparing the sequence of the AH with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for biological activity exhibited by the full-length or mature native sequence.

The variations can be made using methods known in the art and generally involve introducing mutations into the the DNA encoding the AH, followed by expression of the variant AH. Such methods include, for example, oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)], gene shuffling [Stemmer. 1994. Nature 370:389–391 or other known techniques can be performed on the cloned DNA to produce the AH variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081–1085 (1989)]. Alanine is also typically preferred because it is the most common amino acid. Further, it is frequently found in both buried and exposed positions (Creighton, *The Proteins,* (W. H. Freeman & Co., N.Y.); Chothia, *J. Mol. Biol.,* 150:1 (1976)]. If alanine substitution does not yield adequate amounts of variant, an isosteric amino acid can be used.

Covalent modifications of AH are included within the scope of this invention. One type of covalent modification includes reacting targeted amino acid residues of an AH polypeptide with an organic derivatizing agent that is capable of reacting with selected side chains or the N- or C-terminal residues of the AH. Derivatization with bifunctional agents is useful, for instance, for crosslinking AH to a water-insoluble support matrix or surface for use in the method for purifying anti-AH antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl propionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the alpha-amino groups of lysine, arginine, and hisbidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the AH polypeptide included within the scope of this invention comprises altering the native glycosylabon pattern of the polypeptide. "Altering the native glycosylation pattern" is intended for purposes herein to mean increasing or decrease one or more carbohydrate moieties in AH (either by removing the underlying glycosylabon site or by deleting the glycosylation by chemical and/or enzymatic means), and/or adding one or more glycosylation sites that are not present in the native sequence AH. In addition, the phrase includes qualitative changes in the glycosylation of the native proteins, involving a change in the nature and proportions of the various carbohydrate moieties present.

Addition of glycosylabon sites to the AH polypeptide may be accomplished by altering the amino acid sequence. The alteration may be made, for example, by the addition of, or substitution by, one or more serine or threonine residues to the native sequence AH (for O-linked glycosylation sites). Similarly, alteration in N-linked glycosylation can occur by altering one or more invariant amino acids of the Asparagine-X-Serine or Asparagine-X-Threonine sites. Generally, the AH amino acid sequence may be altered through changes at the DNA level, particularly by mutating the DNA encoding the AH polypeptide at preselected bases such that codons are generated that will translate into the desired amino acids, as described above.

Another means of increasing the number of carbohydrate moieties on the AH polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the AH polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of AH comprises linking the AH polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The AH of the present invention may also be modified in a way to form a chimeric molecule comprising AH fused to another, heterologous polypeptide or amino acid sequence.

In one embodiment, such a chimeric molecule comprises a fusion of the AH with a tag polypeptide which provides an epitope to which an antitag antibody can selectively bind. The term "epitope tagged" when used herein refers to a chimeric polypeptide comprising an AH polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues). The epitope tag is generally placed at the amino- or carboxyl- terminus of the AH. The presence of such epitope-tagged forms of the AH can be detected using an antibody against the tag polypeptide. Also, provision of the epitope tag enables the AH to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*,5:3610–3616 (1985)]; and the Herpes Simplex virus glycoprotein D (gD) tag and its antibody [Paborsky et al., *Protein Engineering*, 3(6) :547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an alpha-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

The AH polypeptides and variants of the present invention can be formulated according to known methods to prepare compositions useful in the methods of the present invention, whereby the AH product hereof is combined in admixture with a pharmaceutically acceptable carrier vehicle. Formulations are prepared for storage by mixing the AH having the desired degree of purity with optional physiologically acceptable carriers, excipients or stabilizers (*Remington's Pharmaceutical Sciences* 16th edition, Osol, A. Ed. (1980)), in the form of lyophilized formulations, aqueous solutions or capsular form. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG. Sterilization, when desired, is accomplished by filtration through sterile filtration membranes, prior to or following lyophilization and reconstitution.

The route of administration is in accord with known methods. When the route of administration is oral, the AH is preferably provided as an enteric coated feeds which resist digestion in the stomach and allow release an absorption of AH in the intestine.

Dosages and desired AH concentrations of compositions of the present invention may vary depending on the particular use envisioned. The determination of the appropriate dosage or route of administration is well within the skill of an ordinary artisan.

The present invention further provides anti-AH antibodies. The term "antibody" includes antibody fragments, as are known in the art, including Fab, Fab$_2$, single chain antibodies (Fv for example), chimeric antibodies, etc., either produced by the modification of whole antibodies or those synthesized de novo using recombinant DNA technologies.

In a preferred embodiment, the antibodies to an AH polypeptide upon binding to an AH polypeptide reduce or eliminate at least one biological function of the AH polypeptide as described herein. That is, the addition of anti-AH polypeptide antibodies (either polyclonal or preferably monoclonal) to AH polypeptides (or cells containing AH polypeptides) may reduce or eliminate an AH polypeptide activity. Generally, at least a 25% decrease in activity is preferred, with at least about 50% being particularly preferred and about a 95–100% decrease being especially preferred.

In a preferred embodiment, the AH antibodies of the invention specifically bind to AH polypeptides. By "specifically bind" herein is meant that the antibodies bind to the protein with a binding constant in the range of at least $10^{-4}$–$10^{-6}$ $M^{-1}$, with a preferred range being $10^{-7}$–$10^{-9}$ $M^{-1}$. Antibodies are further described below.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

In a preferred embodiment, the antibody is an Fv fragment. "Fv" is the minimum antibody fragment which contains a complete antigen recognition and binding site. This region consists of a dimer of one $V_H$ and one $V_L$ domain in tight, non-covalent association. It is in this configuration that the three CDRs of each variable domain interact to define an antigen binding site on the surface of the $V_H$–$V_L$ dimer. Collectively, the six CDRs confer antigen binding specificity to the antibody. However, even a single variable domain (or half of an Fv comprising only three CDRs specific for an antigen) has the ability to recognize and bind antigen, although generally at a lower affinity than the entire binding site.

In a preferred embodiment, the antibody is an Fab fragment. Papain digestion of antibodies (or recombinant technologies) produces two identical antigen-binding fragments, called "Fab" fragments, each with a single antigen-binding site, and a residual "Fc" fragment, a designation reflecting the ability to crystallize readily. Accordingly, each Fab fragment is a heterodimer comprising an L chain and a second polypeptide comprising the $V_H$ and $C_H1$ domains. In contrast, the "Fc" fragment is the portion of the antibody that is the ligand of the Fc receptor and does not contain an antigen binding domain. Fc is a disulfide linked homodimer comprising two identical carboxy terminal portions of the antibody H chains.

In a preferred embodiment, the antibody is an F(ab')$_2$ fragment. Pepsin treatment of antibody (or recombinant technologies) yields an F(ab')$_2$ fragment that has two antigen-combining sites and is still capable of cross-linking antigen.

In a preferred embodiment the antibody is an Fab' fragment. By "Fab'" fragments differ from Fab fragments in that the Fab' fragment contains a few residues at the carboxy terminus of the heavy chain $C_H1$ domain including one or more cysteines from the antibody "hinge region". Fab'-SH is the designation herein for Fab' in which the cysteine residue (s) of the constant domains bear a free thiol group. F(ab')$_2$ antibody fragments originally were produced as pairs of Fab' fragments which have hinge cysteines between them. Other chemical couplings of antibody fragments are also known.

In a preferred embodiment, the antibody is a linear antibody. By "linear antibody" herein is meant a linear(L-) F(ab')$_2$, comprising tandem repeats of a heavy chain fragment, $V_H$-$C_H1$-$V_H$-$C_H1$, cosecreted with a light chain (Zapata et al. 1995. Protein Eng. 8(10):1057–1062, which is expressly incorporated by reference).

In a preferred embodiment, the antibody is a scFV antibody. "Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269–315 (1994), all of which are expressly incorporated by reference.

In a preferred embodiment, the antibody is a diabody. The term "diabody" refers to small antibody fragments with two antigen-binding sites, which fragments comprise a heavy-chain variable domain ($V_H$) connected to a light-chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Nag. Acad. Sci. USA, 90:6444–6448 (1993), all of which are expressly incorporated by reference.

Bispecific antibodies are monoclonal antibodies that have binding specificities for at least two different antigens. In the present case, one of the binding specificities is for the AH polypeptide, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl4-mercaptobutyrimidate and those disclosed, for example, in U.S. Pat. No. 4,676,980.

In one embodiment, the anti-AH antibodies may comprise polyclonal antibodies. Methods of preparing polyclonal antibodies are known to the skilled artisan. Polyclonal antibodies can be raised in, for example, a mammal, by one or more injections of an immunizing agent and, if desired, an adjuvant Typically, the immunizing agent and/or adjuvant will be injected in the mammal by multiple subcutaneous or intraperitoneal injections. The immunizing agent may include the AH polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TOM adjuvant (monophosphoryl Lipid A, synthetic trehalose dicorynomycolate). The immunization protocol may be selected by one skilled in the art without undue experimentation.

The anti-AH antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the AH polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The anti-AH antibodies of the invention have various utilities. For example, anti-AH antibodies may be used, for example, in detecting AH expression in specific cells, tissues, or animals. Various assay techniques known in the art may be used, such as competitve binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem, and Cytochem.*, 30:407 (1982).

Anti-AH antibodies also are useful for the affinity purification of AH from recombinant cell culture or in vitro culture of AG tissue as described herein. In this process, the antibodies against AH are immobilized on a suitable support, such a Sephadex resin or filter paper, using methods well known in the art. The immobilized antibody then is contacted with a sample containing the AH to be purified, and thereafter the support is washed with a suitable solvent that will remove substantially all the material in the sample except the AH, which is bound to the immobilized antibody. Finally, the support is washed with another suitable solvent that will release the AH from the antibody.

The invention further provides methods to identify agents etc, that bind and preferably modulate an AH biological activity in the methods of the present invention.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^8$, preferably at least $10^7$, more preferably at least $_{10}8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et a., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.,* 114:1895 (1992); Meier, et al., *Chem. Int. Ed. Engl.,* 31:1008 (1992); Nielsen, *Nature,* 365:566 (1993); Carlsson, et al., *Nature,* 380:207 (1996), all of which are incorporated by reference)). Other analog nucleic acids include those with positive backbones (Denpcy, et al., *Proc. Natl. Acad. Sci. USA,* 92:6097 (1995)); non-ionic backbones (U.S. Pat. Nos. 5,386,023; 5,637,684; 5,602,240; 5,216,141; and 4,469,863; Kiedrowski, et al., *Angew. Chem. Intl. Ed. English,* 30:423 (1991); Letsinger, et al., *J. Am. Chem. Soc.,* 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.,* 4:395 (1994); Jeffs, et al., *J. Biomolecular NMR,* 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev., (*1995) pp.169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d). and e), as well as linker sequences as needed.

In one embodiment of the methods described herein, portions of AH polypeptides are utilized; in a preferred embodiment, portions having AH polypeptide activity are used to identify agents that bind to AH polypeptide. In addition, the assays described herein may utilize either isolated AH polypeptide or cells comprising the AH polypeptide.

Generally, in a preferred embodiment of the methods herein, for example for binding assays, the AH polypeptide or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, TEFLON™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the AH polypeptide is bound to the support, and a candidate bioactive agent is added to the assay. Alternatively, the candidate agent is bound to the support and the AH polypeptide is added. Novel binding agents include specific antibodies, non-natural binding agents identified in screens of chemical libraries, peptide analogs, etc. Of particular interest are screening assays for agents that have a low toxicity for eukaryotic and/or prokaryotic cells. A wide variety of assays may be used for this purpose, including labeled in vitro protein-protein binding assays, electrophoretic mobility shift assays, immunoassays for protein binding, functional assays, preferably the induction of masculinization of female shrimp or prawns.

The determination of the binding of the candidate bioactive agent to the AH polypeptide may be done in a number of ways. In a preferred embodiment, the candidate bioactive agent is labelled, and binding determined directly. For example, this may be done by attaching all or a portion of the AH polypeptide to a solid support, adding a labelled candidate agent (for example a radio or fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}I$, or with fluorophores. Alternatively, more than one component may be labeled with different labels; using $^{125}I$ for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. AH polypeptide), such as an antibody, peptide, binding partner, ligand, etc. Under certain circumstances, there may be competitive binding as between the bioactive agent and the binding moiety, with the binding moiety displacing the bioactive agent. This assay can be used to determine candidate agents which interfere with binding between AH polypeptides and binding partners. "Interference of binding" as used herein means that native binding of the AH polypeptide differs in the presence of the candidate agent. The binding can be eliminated or can be with a reduced affinity. Therefore, in one embodiment, interference is caused by, for example, a conformation change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient Excess reagent is generally removed or washed away. The second component is then added, and the presence or absence of the labeled component is followed, to indicate binding.

In a preferred embodiment, the competitor is added first, followed by the candidate bioactive agent Displacement of the competitor is an indication that the candidate bioactive agent is binding to the AH polypeptide and thus is capable of binding to, and potentially modulating, the activity of the AH polypeptide. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the AH polypeptide with a higher affinity. Thus, if the candidate bioactive agent is labeled, the presence of the label on the support, coupled with a lack of competitor binding, may indicate that the candidate agent is capable of binding to the AH protein.

In a preferred embodiment, the methods comprise differential screening to identity bioactive agents that are capable of modulating the activity of the AH polypeptides. Such assays can be done with the AH polypeptide or cells comprising said AH polypeptide. In one embodiment, the methods comprise combining an AH polypeptide and a competitor in a first sample. A second sample comprises a candidate bioactive agent, an AH polypeptide and a competitor. The binding of the competitor is determined for both samples, and a change, or difference in binding between the two samples indicates the presence of an agent capable of binding to the AH polypeptide and potentially modulating its activity. That is, if the binding of the competitor is different in the second sample relative to the first sample, the agent is capable of binding to the AH polypeptide.

Alternatively, a preferred embodiment utilizes differential screening to identify candidates agents that bind to the native AH polypeptide, but cannot bind to modified AH polypeptides. The structure of the AH polypeptide may be modeled, and used in rational drug design to synthesize agents that interact with that site. Drug candidates that affect AH bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate an activity of an AH polypeptide may also be done. In a preferred embodiment, methods for screening for a bioactive agent capable of modulating the activity of AH comprise the steps of adding a candidate bioactive agent to a sample of an AH polypeptide (or cells comprising an AH) and determining an alteration in the biological activity of the AH polypeptide. "Modulating the activity of an AH polypeptide" includes an increase in activity, a decrease in activity, or a change in the type or kind of activity present Thus, in this embodiment, the candidate agent should both bind to AH polypeptide (although this may not be necessary), and alter its biological or biochemical activity as defined herein. The methods include both in vitro screening methods, as are generally outlined above, and in vivo screening of cells for alterations in the presence, distribution, activity or amount of AH polypeptide.

Thus, in this embodiment, the methods comprise combining an AH sample and a candidate bioactive agent, and evaluating the effect on the AH activity. By "AH activity" or grammatical equivalents herein is meant one of the AH polypeptide's biological activities, including, but not limited to, its ability to induce masculinization in genetic female shrimp or prawns.

In a preferred embodiment, the activity of the AH polypeptide is decreased; in another preferred embodiment, the activity of the AH polypeptide is increased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of an AH polypeptide. The methods comprise adding a candidate bioactive agent, as defined above, to a cell comprising AH polypeptides. Preferred cell types include almost any cell. The cells contain a recombinant nucleic acid that encodes an AH polypeptide. In a preferred embodiment, a library of candidate agents are tested on a plurality of cells.

A change or modulation in AH activity, which can be an increase or decrease in activity, is preferably a change of at least 20% to 50%, more preferably by at least 50% to 75%, more preferably at least 75% to 100%, and more preferably 150% to 200%, and most preferably is a change of at least 2 to 10 fold compared to a control. Accordingly, in one embodiment a modulator of the present invention is identified by treating a female shrimp or prawn with AH polypeptide and the candidate agent or candidate modulator and measuring the affect of the co-treatment on sex-reversal, the development of neomales, and their capacity to produce sex-skewed populations comprising predominantly female progeny, as compared females treated with AH polypeptide in the absence of the candidate agent.

All patents, patent application, references, and publications cited in the present specification are hereby incorporated by reference in their entirety.

The following examples are offered for illustrative purposes only, and are not intended to limit the scope of the present invention in any way.

EXAMPLES

Example 1

Secretion of Androgenic Sex Hormone (AH)

Mature fresh water male prawns (*Macrobrachium rosenbergii*) with a mass of 50–90 grams, were obtained from a commercial farm (Hawaiian FarmFresh Seafood, LLC, Kahuku, Oahu, Hi.) and were reared in a flow-through fresh water system at 21° C. (+/−3° C.) for more than one week before use. Prawns were fed the commercially available Rangen Shrimp diet which is 40 percent protein. Twenty-five freshly dissected AGs were placed into a sterile/gamma irradiated petri dish (Becton Dickinson), containing 300 ml of defined medium (188 mM NaCl, 13 mM $CaCl_2 2H_2O$, 7 mM KCl, 10 mM $MgSO_4 7H_2O$, 2 mM $NaHCO_3$, pH 7.6). The petri dishes were placed in a moist, modulator incubator chamber (Billups-Rothenberg, Inc.) at 25° C. The release of AH(s) from the AGs into the medium was determined through sodium-dodecyl sulfate polyacrylamide gel electrophoresis (SDS-PAGE). At the termination of incubation (2, 4, and 8 hours), the AGs and medium were separated by brief centrifugation at 5000 g (Eppendorf). The secreted hormone(s) in the culture medium were desalted and concentrated with a Microcon centrifugal filter device (Amicon) and the AGs were homogenized in 300 ml of culture medium and centrifuged to produce a whole cell-free homogenate. The secreted proteins and the cell-free homogenate were then subjected to SDS-PAGE immediately or quick frozen in a dry icelethanol bath and stored at −80° C. until analyzed (Malecha et al. (1992) Aquaculture 105:1–18; Nagamine et al. 1980. Gen. Comp. Endocrin. 41:423–441). (see FIG. 1)

Example 2

SDS-PAGE Analysis of Secreted AH

AH samples from Example I were subjected to SDS-PAGE using the buffer system of Laemmli (1970) Nature 227:680–685 and the procedures were as described by Sambrook, et al. (1989). Samples were run on vertical slab gels consisting of 5% acrylamide stacking gel and 15% acrylamide running gel (13 cm×16 cm). The samples were run for 4 hours at a constant voltage of 11 volts using a power supply (EC-103 Apparatus Corporation). After electrophoresis, the gel was stained overnight in 0.25% Coomassie Blue R-250 in methanol:acetic acid water (45:45:10). The gel was de-stained at room temperature in a solution of methanol:acetic acid:water (1:2:17). The de-stained gel was dried with a slab gel drier (Model SGD 4050, Savant) and the gel was photographed. As shown in FIG. 1, bands of ~8-Kd, ~13-Kd, ~14-Kd, ~16-Kd, ~18-Kd, and ~23–26-Kd are observed, wherein at least the 16 and 18 Kd bands are the AH polypeptides.

Example 3

Amino Acid Analysis of AH

An SOS-PAGE analysis similar to Example 2 was performed according to the aforementioned procedures. After electrophoresis completion, the proteins bands were transferred to a PVDF protein transfer and sequencing member (Schleicher and Schuell). The PVDF membrane was stained with Ponceaus S solution (2 g Ponceau S, 30 g sulfosalicylic acid, and water to 1 liter) and de-stained with distilled water. The 16-Kd and 18-Kd bands are subsequently excised from the membrane, air dried, and the sequence is determined and confirmed by any one or more of the following procedures: (i) N-terminal amino acid sequencing; (ii) C-terminal amino acid sequence; (iii) enzymatic digestion and terminal sequencing of fragments; (iv) mass spectroscopy analysis of AH polypeptide and enzyme prepared fragments by MALDI-TOF (matrix-assisted laser desorption ionizadon-time of flight analysis (Taketomi et al. 1998. Acta Biochem Pot. 45(4):987–999; de Jong. 1998. Mass Spectrom. Rev. 17(5):311–335; Lin et al. 1998.Comp. Biochem. Physiol. A. Mol. Integr. Physiol. 121(4):315–321).

Example 4

Sex-Reversal by Injection of Androgenic Hormone
Setup and Termination.

All initial setup activities were conducted within a ten hour period to insure the freshness and congruity of the application of the AG material. These setup activities included obtaining the secretion material by the AG explant method described above (Example 1) and the injection of the secretion material into hosts to create the main "secretion injection" group. The implantation of the AG material into control hosts, the injection of sham controls and the setup of the null control group occurred on a subsequent day. All surviving animals in the compartmentalized aquaria, described below, were sexed by means of a check of the live animals. The surviving secretion injection animals were transferred to individual 2 gallon aquaria for additional growth. All three surviving secretion animals were sacrificed, measured for length, weight and external sexual characteristics.

Sexing of Prawn Hosts

Candidate prawn female hosts for the injection, implantation, and control groups were drawn from a pool of potential female prawn hosts averaging 3.66 cm length measured as the shortest distance from the posterior eyestalk orbit to the Up of the uropod tail appendage. The sex of candidate hosts was determined about 1–7 days prior to initiation of sex reversal. The candidate hosts were sexed as female by examining unsexed animals from a mixed sex population obtained from commercial sources and housed in aquaria tanks in the lab. The female sex determination was based on the assessment of the absence of a male appendix masculina on the base of the second pleopod on the candidate hosts following the description of the appendix masculina development and the sexing process described in Tombes and Foster(1979) Crustaceana Suppl 5. pp:179–184. Growth of appendix masculina and appendix interna in juvenile *Macrobrachium rosenbergii* (de Man) (Decapoda, Caridea); Nagamine, C. and A. W. Knight. (1980). Development, maturation, and function of some sexually dimorphic structures of the Malaysian prawn *Macrobrachium rosenbergii* (de Man) (Decapoda, Plaemonidae) Crustaceana 39(2):141–152. ; and Malecha et al. 1992a. This sexing process was also used to assess the neomale sex reversal process in the injectees (see below).

Dissection of the Prawn Androgenic Gland (AG)

Dissection of prawn AG was done as described in Example 1 and by Malecha et al. (1992) Aquaculture 105:1–18 and Nagamine et al. (1980) Gen. Comp. Endocrin. 41:423–441.

Preparation of the Secretion Material for Injection into Sexually Immature Female Hosts This follows the procedure of Example 1. Sixty (60) freshly dissected fresh water prawn androgenic glands (AGs) were placed into the sterile gamma irradiated petri dish containing the defined media as described in Example. The AGs were left to incubate in the media for six (6) hours in a moist, modular incubator (Billuos-Rothenberg) at 25° C. The entire media solution containing the AG themselves and the secreted AG proteins was then collected by pipette and transferred into microcentrifuge tubes. The tubes were immediately brought to a cold room at about 4° C. where they were centrifuged for 1 hour at 5000 g through a microcon centrifugal filter device (Millipore Corporation) to separate all proteins as large as, and smaller than, 3000 daltons (3 kd) in molecular weight from the larger AG protein concentrate which included the AH. The microcentrifuge tubes containing the AG protein concentrate were kept on ice for use as soon as possible as the source of the injectates into host prawn females (injectees). The volume of the resulting concentrated solution was sufficient to inject into approximately 8–10 host female prawns so that approximately 2.5 microliters of injectate would contain the equivalent of an "AG dosage" of two androgenic glands.

Secretion Injection Experimental Group

Aliquots of 2.5 microliters of the AG protein concentrate were drawn into a sterilized (10) microliter syringe tipped with a 21 gauge needle by the person performing the injection ("injector"). Female prawn hosts were netted from a holding container by an assistant to the injector and held securely, but lightly, by the assistant between his/her thumb and forefinger of one hand so that the ventral side of the host was exposed upward. With the other hand, the assistant spread apart the fourth and fifth walking legs and the first pleopods of the host with a blunt probe and/or the assistant's free hand in such a way as to clearly expose, to the injector, the ventral area between the fifth walking leg and the first pleopod. The injector then pushed the needle tip of the syringe into soft area between the fifth walking leg and the first tail segment so as to enter a void, hemocoelic, space internal to the host. The object of this procedure was to probe the needle into a void space in the host's body through the soft integument and not through hardened exoskeleton (chitin) material. In some case the injection probe was made into muscle.

Once the needle was inserted and little or no back pressure was felt indicating a "good" insertion, the needle plunger was advanced by the injector and the AG protein concentrate was delivered into the host's body. The injected host was then immediately transferred to an aquarium compartment for observation and its subsequent growth as described below. The injection procedure was performed as rapidly as possible in an air conditioned animal holding room(24–26° C.) to minimize trauma to the host and to achieve delivery of the injectate in one "try" if possible. Therefore, the presentation of the host by the assistant to the injector and the injection itself was done in a parsimonious series of motions. Nine hosts were injected with the AG protein concentrate. These animals constituted the primary animal group collectively identified in the results Tables 1 and 2 as the "secretion injection" group.

AG Implantation Control Group

Sixteen (16) female hosts, obtained from the same pool of female-sexed animals as the "secretion injection" group hosts were implanted with AG tissue following the procedures described in Nagamine et al., 1980b and Malecha et al., 1992a. The implanted AG tissue was obtained from freshly dissected AGs obtained in the same manner as described for obtaining the AGs for the secretion work. An attempt was made to dissect the AG cleanly from surrounding tissue but small amounts of such tissue still clung to the AG so that the material implanted into the host is hereafter referred to as "AG tissue". Once dissected from a male donor, the AG tissue was immediately placed into a saline solution of the same composition as the media described above for the secretion. After about 10 minutes or less, the AG tissue was removed from this medium and implanted, by a second person, into the host recipient. Implantation was done by first making a "probe incision" with a sharp probe into the host in the same ventral area that was the target for the secretion injections. The AG tissue was then inserted, i.e. "pushed", into the recipient host through the probe incision by a second blunt probe or sharp forceps that were grasping the AG tissue. Once implanted, the hosts were immediately transferred to an aquarium compartment for observation and further growth.

Sham Injection Control Group

One control group consisted of five (5) hosts receiving only a probe with the needle tipped onto an empty syringe. This constituted a "sham" injection control group. The sham injection was made in a manner identical to the that described for the secretion injections but the syringe plunger was not advanced and no material was delivered to the hosts.

Null Injection Control Group

One control group, "null" controls, consisted of five (5) hosts receiving no AG material challenges or sham injections.

Husbandry of Experimental and Control Groups

Each injectee and control animal was placed into a compartment in a four (4) compartment three (3) gallon glass aquarium. The four compartments were created by three partitions made of a rigid plastic grid material over which window screen had been affixed. The partitions were kept in place perpendicular to the long axis of the rectangular aquarium by the tension created by sections of a rubber garden hose slit open and fitted snugly between the vertical sides of the partition and the aquarium wall. The bottom of the partition was buried into a gravel layer on the bottom of the aquarium. The gravel overlaid the grid of an under gravel filter system powered by two air lift pumps at either end of the aquarium. The components of this sunder gravel airlift aeration system is readily available from commercial aquarium supply vendors. This provided aeration to the aquarium and water movement downward through the gravel which acted like a mechanical and biological filter. The water level was kept below the top of the partitions to minimize the jumping of the animals between compartments. The airlift excurrent ports was above the water line. Water in the aquaria was exchanged with freshwater about every 6–8 days or as it began to get cloudy or develop an odor. Four compartmentalized aquaria were placed on blocks in a larger tank containing 60–75 gallons of water. This larger tank provided a water bath environment to the compartmentalized aquaria. A commercial immersion aquarium heater was placed in the water bath and adjusted to kept the water bath and the aquarium water at 260–28° C. The water bath tanks were located in an air conditioned animal holding room.

Experimental and control animals were checked each day for general health and the presence of an molted exoskeleton ("exuvium") indicating that the animal had molted. An exuvium is a replica of sufficient anatomical detail of the living animal's external body by which sexual determination is routinely made in the art A molted exuvium was collected from the compartment and immediately examined for the evidence of the development of a male appendix masculina on the base of the second pleopod. In developing normal males and sex reversed neomales, the appendix masculina can make its first appearance as a "bud" between the appendix internal and the segment of the second pleopod on an exuvium. (FIG. 3). Subsequent exuvia display elongated appendix masculina buds or the appendix masculina itself which grows in length as on subsequent exuvia of an animal's molting sequence. Females, such as those in the sham and null control groups do not display the appendix masculina. The exuvia collected from all molted animals were preserved in alcohol in containers labeled with the date and the animal identification.

Results

Table 1 presents the primary results of the secretion injection experiment. Five animals, two (2) in the secretion injection group and three (3) in the implantation control group, died too early in the experiment (most likely to the initial surgical trauma of the AG material challenge) to be scored in the experiment. Only animals surviving long enough to molt twice and provide at least two exuvia were scored as "positive" or "negative" for neomale masculinization. As seen in Table 1, six (6) out of seven (7) of the injected surviving animals showed the development of an appendix masculina indicating that these animals are neomales masculinized by the AG proteins in the injectate (FIG. 1). Five (5) of the eight (8) implanted surviving animals were masculinized into neomales. As expected, none of the control animals showed neomale masculinization. The thirteen surviving implantation control animals, and the five (5) surviving sham and null control animals (Table 1) were sexed as live animals. These results are presented in Table 1.

In the case of the control animals all were scored as females as expected indicating that it is unlikely the mis-sexing of the secretion injection and implantation hosts occurred at the beginning of the protocol.

TABLE 1

Summary of results of sex reversal by injection of AG secreted material

| Group | Starting Number | Number Dying[a] | Number Surviving | AM+ | AM− |
|---|---|---|---|---|---|
| Secretion Injection | 9 | 2 | 7 | 6 | 1 |
| Implantation Controls | 16 | 3 | 13 | 8 | 5 |
| Null Controls | 5 | 0 | 5 | 0 | 5 |
| Sham controls | 5 | 0 | 5 | 0 | 5 |

[a]number of animals that died too early in the course of the protocol to be examined for *appendix masculina* (AM) development.
AM+: positive for *appendix masculina*.
AM−: negative for *appendix masculina*.

Molting History and Development of Animals in the Secretion Injection Group

Table 2 presents the molt history of the animals in the secretion injection group. As seen in Table 2, six (6) injected animals (nos. 1–6) showed positive neomale masculinization. One (1) injected animal no. 7) did not show evidence of neomale masculinization. All of these animals shown survived at least to the fourth molt, with three animals (nos. 1, 2 and 5) surviving to the termination of the protocol 183 days after it began. Three animals (nos. 2, 3 and 6) showed the development of an appendix masculina "bud" on the their first molted exuvium (indicated by "+b" in the first molt column of Table 2). Two of these animals (nos. 2 and 6) displayed a whole appendix masculina on the next molted exuvium (indicated by the "+am" in Table 2). Three animals (nos 1, 4, 5) had partially eaten their first molt exuvium, (indicated by "p" in Table 1), so that no scoring could be conducted on these exuvia. All three of these animals scored positive for a whole appendix masculina in their second molt. As seen in Table 1, three animals (nos. 1, 2 and 5) survived until the termination of the protocol at which time they were sacrificed and preserved as whole animals in Davidson solution. The mean elapsed time from the beginning of the protocol, and the AG material challenges or control setup and the mean time between the molts is shown at the bottom of Table 2. This data indicates a very consist molt frequency indicative of a normal growth pattern.

Anatomical Evidence of Neomale Masculinization.

FIG. 2 presents a photograph of the "bud" on section injection animal no.3. FIG. 3 shows the bud appearing as a elongated protuberance at the base of the second pleopod between the appendix interna (an appendage present in both males and females) and the endopod segment of the binary segmented pleopod. Although longer than the bud in FIG. 2 it can be compared with the appendix masculina bud in FIG. 3 in Tombes and Foster (1979) supra who were the first to describe the male appendix masculina bud formation in normal prawn males. Five (5) secretion injection animals (nos. 1,2,4,5 and 6) showed a whole appendix masculina by their third molt. All the "positive" secretion injection animals (nos. 1–6) eventually displayed a fully developed masculina which grew to its full length in the three well developed neomales (nos. 1,2 and 5). FIGS. 3, 4, and 5 show a developed appendix masculina. FIG. 6 presents the first molted exuvium, a subsequence molted exuvium and the intact neomale animal sacrificed at the end of the experiment.

Example 5

Induction of Masculinization by Contacting with AH

The following protocol was followed to induce masculinization in the very small marine shrimp, *Penaeus vannemei,* hosts by placing them in small wells containing 4 ml of sea water into which androgenic glands (AGs) are also placed. The hosts were immersed into the material secreted by the AG gland including the masculinizing androgenic hormone, AH. Without being bound by theory, the genetic female hosts takes up, absorbs, or injects the AH from the medium and are sex reversed to neomales. In addition, the genetic female hosts consume the AG tissue as food and may obtain active AH to induce masculinization.

The size of the hosts are too small to sex at the time of the AG immersion challenges so that the masculinization effect is assessed from a sex ratio of males to female which is determined when the hosts are big enough to be sexed accurately. Neomale production will result in a sex ratio skewed in favor of males in the challenged hosts.

Androgenic Gland Dissection and Collection.

The androgenic gland (AG) from male donor marine shrimp was collected using methods similar to those described above for the freshwater prawn AG in Example 1. Large male marine shrimp donors obtained from commercial sources were used. The terminal section of the vas deferens was dissected from the donors and the AG tissue teased from its location on the distal, terminal end of the vas deferens. The AG tissue material was immediately placed in a holding container of sea water (ocean water obtained from Waikiki Aquarium, Hi.) sitting on ice.

Animals

Post larvae ("PL") obtained from a commercial hatchery (Hawaii FarmFresh Seafood)was used in this experiment. PLs are very small juveniles recently developed from the larvae that are reared in commercial hatcheries. The PLs used in the experiment were "P-26s" meaning they were 26 days "old" measured as the time in days from when they developed from the last larval stage to the PL stage. The PLIs were obtained from the commercial source a few days before initiating the protocol and were kept in sea water-filled aquaria in an animal holding facility.

TABLE 2

Molt History of section injection group

| Animal No. | Start (cm) | Number of elapsed days since previous event[1] for each molt observedt: | | | | | | | | | End | | |
|---|---|---|---|---|---|---|---|---|---|---|---|---|---|
| | | 1st | 2nd | 3rd | 4th | 5th | 6th | 7th | 8th | 9th | Day | (cm) | (gm) |
| 1+[a] | 3.90 | 45 p | 66 +am | 95 | 107 | 122 | 135 | 152 | 167 | 182 | 183 | 12.2 | 43 |
| 2+ | 3.50 | 32 +b | 48 +am | 62 | 78 | 107 | 124 | — | — | — | 183 | 10.6 | 25 |
| 3+ | 3.40 | 33 +b | 49 +b | 70 | 85 | 109 | 138 | 156 | 175 | d | | | |
| 4+ | 4.00 | 48 p | 88 +am | 101 | 118 | d | | | | | | | |
| 5+ | 3.50 | 31 p | 44 +am | 59 | 79 | 97 | 110 | 128 | — | — | 183 | 10.5 | 32 |
| 6+ | 4.20 | 13 +b | 26 +am | 35 | 48 | 62 | 78 | d | | | | | |
| 7− | 3.10 | 31 −am | 45 | d | | | | | | | | | |
| mean length = | 3.66 | | | | | | | | | | | | |
| mean elapsed days[2] = | | 33 | 52 | 70 | 86 | 99 | 117 | 145 | 171 | 182 | mean= | 11.1 | 33.3 |
| mean days from previous = | | 33 | 19 | 18 | 16 | 14 | 18 | 28 | 26 | 11 | | | |

+am positive for whole appendix masculina on second pleopod;
−am no evidence of appendix masculina development;
+b positive development of appendix masculina bud (rudimentary am at the initial stages of development (see FIG. 2));
− no further molts were observed; these animals survived until sacrificed at the termination of the protocol;
p partially cannibalized exuvium, am development can not be scored;
d animal died; all animals that died shows the development of the am;
1 event is either the injection of AH or the previous molt;
2 mean elapsed time in days since a previous event to the respective molt; the previous event is the initial injection in the case of the first molt, and the previous molt in the case of all subsequent molts.

Immersion Group

Eighteen (18) PL hosts were first placed in wells containing 4 ml of sterilized sea water. These animal made up the immersion group which was exposed to AG tissue in three "challenges". Each challenge consisted of placing two (2) AG glands which were collected from the holding container described above, within minutes of their dissection and placing the AGs into the well containing one host. Challenge #1 was conducted on the first day of the experiment. Challenge #2 was conducted 36 hours after the first challenge. Challenge #3 was conducted 36 hours after the second challenge. The AG were left in the wells for 24 hours after the challenge and them removed to maintain water quality.

Individually Reared Control Group

Thirty (30) PIs were placed individually into wells containing 4 ml of sea water in a manner identical to that described above for the immersion group. No AG challenges were administered to this group whose sex ratio was compared to the sex ratio of the immersion group.

Communally Reared Control Group

Twenty (20) PIs were reared communally in a plastic beaker set up alongside the well containers. No AG challenges were administered to the communally reared control sex group whose sex ratio was used compared to the well-reared control group. Any deviation of the latter from the former could be considered a function of the well environment.

Husbandry and Growth

Twenty four hours (24) after the third challenge of the immersion group the well reared animals were transferred into individual compartments of a two compartment plastic container containing sea water from a water bath (see below). Each compartment contained small coral substrate rock and each container had screened bottoms and side openings through which water could flow from the water bath. Each container measured approximately 4 inches by 1.5 inches. The compartments were separated from one another by a plastic partition. Each container thereby contained two animals. The small two-compartment containers placed into a larger plastic containers fashioned with a screen bottom to allow water flow through the larger container and thereby through the individual animal containers. Two larger containers were placed into a larger tank containing approximately 75 gallons of sea water in such a way that the water level immersed approximately 80% of the compartment above the top level of the coral substrate. This whole system created a water bath-like environment. A commercial reticulation pump and filter was placed in each tank such that bottom water was collected and returned to the top. All animals were fed an ad libitum amount of commercial shrimp feed once each day. Also each day all animals living in the compartments were checked for general health (as animals become stressed they become less active and develop and opaque appearance) and water quality, as described above. If the health of the animals was decreasing air was bubbled into the water and the water was changed. The water bath temperature was kept at 26°–28° C. with a commercially available aquarium heater as described for the prawn secretion experiment above.

Results

The immersion and control animals were reared until they were approximately 1 inch in length, a size large enough for them to be sexed accurately without stress. Sex was determined by the presence of the external male genitalia on the first pleopod and the presence or absence of the appendix masculina on the second pleopod as described in King, J. E. 1948. A Study of the reproductive organs of the common marine shrimp, Penaeus setiferus (Linnaeus). Biol. Bull. 94:244–262. Table 3 presents a summary of the results. As seen in the table both control groups displayed about a 1:1 sex ratio as expected from a randomly sampled population of mix-sexed animals. The immersion group, however, displayed a sex ratio of about 2:1 skewed in favor of males, indicating that some of the males were sex revered neomales.

TABLE 3

Summary of results of immersion protocol

| Group | Starting Number | Number Dying | Number Surviving | Male (M) | Female (F) | M:F |
|---|---|---|---|---|---|---|
| Immersion | 18 | 8 | 10 | 7 | 3 | 2.3 |
| Individually well-reared controls | 30 | 20 | 9 | 4 | 5 | 0.8 |
| Communally reared controls | 20 | 13 | 7 | 4 | 3 | 13 |
| | | | All controls: | 8 | 8 | 1.0 |

Example 6

Construction of a cDNA Library from a shrimp or prawn AG

The AG from approximately 300 animals (Penaeus vannamei; and M. rosenberuii) is collected as described above. Total RNA is isolated from these glands according to the method of Chomczynski and Sacchi (1987) Anal. Biochem. 162:156–159. Pure mRNA is obtained using the Fast Track 2.0 kit from Invitrogen, Inc. Approximately 4 microgram of pure mRNA is used for construction of a cDNA library from each animal.

The cDNA library is constructed using the ZAP cDNA (Stratagene) system using the protocols of Sambrook et al., 1989. This involves the use of the mRNA isolated from the AG as a template in producing the complementary DNA by reverse transcriptase, and the synthesis of the second strand of DNA by DNA polymerase. The double stranded DNAs are then inserted into an appropriate cloning vector and multiplied in bacteria after transformation.

Example 7

Identification of the Full-Length cDNA encoding the AH polypeptide from the AGDNA Libraries The full-length cDNA encoding the AH polypeptide of prawn or shrimp are obtained by screening the AG-cDNA library with degenerate oligonucleotides as probes which are labeled with digoxigenin-11UTP according to the method described in the Technical Bulletin of Genius non-radioactive system (Boehringer-Mannheim). The strategy of screening will be using a combined method of PCR amplification (Amaravadi and King, (1994) Biotechniques 16:98–104) and the in situ plaque hybridization technique of Benton and Davis (1977) Science 196:180–182.

The sequence of the degenerate oligonucleotide probes is based on the amino acid sequence of the AH of prawn or shrimp obtain according to the methods described herein. Due to the degeneracy of the genetic code, multiple or degenerate probes are synthesized to contain all possible permutations of the nucleic acid sequence that may encode the AH amino acid sequence of prawns or shrimp.

Approximately $1 \times 10^6$ recombinant clones are plated on 20 (150 mm) plates and incubated for 10 hours at 37° C. or until plaques begin to contact each other. The ZAP XR phages (Stratagene) are soaked in 10 ml of phage diluted buffer (NaCl, 5.8 g; $MgSO_4 7H_2O$, 2 g; 1 M Tris-HCl, pH 7.5, 50 ml; 2% gelatin solution, 5 ml; $H_2O$ to 1 liter) overnight at 4° C. The phage dilution buffer (PDB) is collected from each plate and centrifuged at 5,000×g for 10 minutes to remove debris. E. coli will be lysed by adding a few drops of $CHCl_3$ An aliquot of 1 ul of plate lysate is used as the template for PCR assay. The PCR protocol is performed as previously described (Sun, (1994) Mol. Mar. Biol. Biotechnol. 3(1):1–6 and the PCR products are first analyzed by agarose gel electrophoresis.

The detection of an expected mass of DNA product indicates a positive AH polypeptide clone in the plate lysate. Once a positive plate lysate is identified, several rounds of replating and PCR amplification lead to the identification of individual positive plaques. Individual positive AP-containing plaques are further confirmed by plaque hybridization as described by Sambrook et al. (1989) using the oligotide AHcDNA primer probe labeled with digoxigenin-11-UTP. The sensitivity and reliability of plaque hybridization will prove that a positive AH polypeptide clone is obtained.

The Wizard Lambda Preps DNA purification system from Promega (Wisconsin) is used for purification of the phagemid DNA from the positive clone(s). The gel-cleaned phagemid DNA is subjected to Southern analysis. After electrophoresis, the DNAs are transferred to Hybone-N-membrane (Amersham). Hybridization will be performed at 32° C. for 20 hours with a Dig-labeled cDNA probe. The hybridzation solution will contain 40% formamide, 0.1% (w/v) sodium-N-lauroylsarcosine, 7% (wlv) SDS, 250 mM sodium phosphate buffer (pH 7.2), 1 mM EDTA, and 1% (w/v) BSA The probes are labeled with digoxigenin-11-UTP according to the Technical Bulletin of Genius non-radioactive system (Boehringer-Mannheim). After washing, the positive hybridization bands can be identified by immunological reaction as described in the Boehringer-Mannheim detection kit. Detailed procedures of non-radioactive hybridization have been described in Sun (1994) supra, and Sun (1995) *Mol. Mar. Biotechnol.* 4(3):262–268.

Positive clones having the largest size of DNA as revealed by Southern blotting are selected and their DNAs multiplied in *E.coli* purified, and the DNAs is further characterized by sequencing (Sanger et al., (1977) Proc. Natl. Acad. Sci. USA 74:5463–5467) and physical mapping (Sambrook et al., 1989). The deduced amino acid sequence of the cloned AH polypeptide is analyzed and compared with published data from other species using the Best-Fit Program (Genetics Computer Group, Madison, Wis.) and the Fuchsia Program available from the Computer Center at the University of Hawaii.

Example 8

Recombinant AH Expression in Yeast

An AH polypeptide expression vector is constructed by first modifying the full length AH-cDNA by creating two restriction sites, a SnaB1 at the 5' end and a Not1 the at 3' end, using the polymerase chain reaction method (PCR). The modified cDNA is then sub-cloned into the expression vector pPIC9 (Invitrogen, California) which contains an alpha factor secretion signal derived from *Saccharomyces cerevisiae* and a HIS gene for selection of transformants of the yeast *Pichia pectoris*.

Approximately one mg of pPIC9-AH DNA is digested with BgIII to produced a linear AH DNA molecule with ends homologous to the 5' and 3' termini of the alcohol oxidase gene (AOX1), whose product is involved in the process of methanol metabolism. Integration into the host yeast cell AOX1 locus occurs by double crossover recombination resulting in the complete removal of the AOX1 coding region and, consequently, the loss of the ability to utilize methanol efficiently. The linearized DNA is used to transform the yeast *P. pastoris* strain GS115 (his4) to the His$^+$ phenotype by the electroporation method described in Scorer et al., ( 1994) Bio/technology 12:181–184.

Transformation is performed by electroporation using an electroporation (Invitrogen, California) One millimeter of cold 1 M sorbitol is added to the cuvettes immediately after pulsing, and 200–600 ml aliquots is spread on minimal dextrose plates (MD plates, containing 1.34% yeast nitrogen base, $4 \times 10^{-5}$% biotin, 1% dextrose and 15 g agar per liter). His$^+$Mut$^s$ transformants are screened by patching on minimal dextrose (MD) verus minimal methanol (MM) plates as described in the manufacturer's (Invitrogen) instruction. (This entails the same ingredients as in MD plates except that 1% dextrose is replaced by 0.5% methanol).

Colonies showing slow growth on methanol are recovered and grown in 10 ml YPD medium (1% yeast extract, 2% peptone, and 2% glucose) for 2 days at 30° C. Cells from each colony culture are collected by centrifugation at 1500×g for 5 minutes at room temperature and re-suspended in 2 ml of fresh SCED buffer (1M sorbitol, 10 mM sodium citrate, pH 7.5, 10 mM EDTA, 10 mM DTT) to be used for genomic DNA isolation. Isolation of genomic DNA from the selected His$^+$ Mut$^s$ Pichia clones is done using the Easy-DNA kit from Invitrogen Corporation (California). The genomic DNA is used as templates for PCR amplification in order to identify if the AH polypeptide gene has integrated into the Pichia genome. PCR amplification is carried out on the Perkin-Elmer 9600 thermal cycler and a pair of 5' and 3' AOX1 primers (5' AOX1:5'GGACTGGTTCCAATTGACAAGC 3' (SEQ ID NO:1); 3' AOX1:5'GCAAATGGCATTCTGACATCC 3' (SEQ ID NO:2)) are used. A DNA band of correct size indicates that the AH polypeptide gene has integrated into the Pichia genome.

The transformant showing the highest yield of AH polypeptide from mini-culture experiments are chosen to use for large-scale fermentation. To do this a 100-ml culture of GS115-AH transformant is grown in a 1000-ml baffled shake flasks at 30° C. shaking at 250–300 rpm for 20 hours (or O.D.=6) on BMGY medium. The latter is composed of 1% yeast extract, 2% peptone, 100 mM potassium phosphate, pH 6.0, 1.34% yeast nitrogen base, $4 \times 15^{-5}$% biotin and 1% glycerol. To induce AH expression, cells are harvested by centrifugation at 1500×g for 5 min at room temperature and re-suspended in ⅕ of the original culture volume of BMMY medium (this is the same as the BMGY medium except that 1% glycerol was replaced by 0.5% methanol). The induction phase is maintained for 8–10 days with 100% methanol added to a final concentration of 0.5% very 24 hours. One milliliter samples are withdrawn from the culture medium every 24 hours for protein expression analysis. Following centrifugation to remove the cell pellets from the culture medium, the supernatant from each sample is kept at −80 C. until use.

Samples of the secreted expression from *P. pastoris* GS115 host strain in the culture supernatant is subjected to SDS-polyacrylamide gel electrophoresis (SDS-PAGE) and Western blot analysis. SDS-PAGE is performed based on the methods of Davis (1964) and Laemmli (1970), with a 15% separation gel and a 4% stacking gel. Polypeptides separated by SDS-polyacrylamide gels are fixed with methanol/glacial acetic acid and stained with Coomassie Brilliant Blue R250 (Sambrook et al., 1989). Protein mass standards of Rainbow markers (Amersham, Ill.) are co-run in the gel electrophoresis. For Western blotting, the methods of Towbin et al. (1979) Proc. Natl. Acad. Sci. USA 76:4350 and Bumette (1981) Anal. Biochem. 112:195 are followed. This consists of transferring the separated protein, after gel electrophoresis, to a pure nitrocellulose 0.05 mm pore sized immobilization membrane (Schleicher and Schuell, New Hampshire) treated with anti-AH polyclonal antibodies (Sedberry and Sun, (1997) *Penaeus vannamei. Biol. Bull.* (submitted)) followed by goat anti-rabbit IgG conjugated to horseradish peroxidase. The membrane is then developed with ECL reagents (Amersham, Ill.), and exposed to X-ray film (Fuji, Tokyo).

The recombinant AH polypeptide secreted from the culture medium is purified by large scale and analytical scale column chromatography and high pressure liquid chromatography. Following purification the recombinant AH is subjected to bioassay described above in for prawns or shrimp.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. All patents, patent applications, publications, and references cited herein are hereby expressly incorporated by reference in their entirety.

What we claim is:

1. A method of producing a population of shrimp or prawns having a skewed percentage of females to males, comprising:

breeding a neomale shrimp or prawn which does not contain transplanted androgenic tissue with a corresponding female shrimp or prawn, whereby a population of shrimp or prawns having a skewed percentage of females to males is produced.

2. The method of claim 1, wherein said percentage of females is greater than about 80%.

3. The method of claim 1, wherein said percentage of females is greater than about 90%.

4. The method of claim 1, wherein said percentage of females is 100%.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial sequence
<220> FEATURE:
<223> OTHER INFORMATION: primer

<400> SEQUENCE: 1
ggactggttc caattgacaa gc                                              22

<210> SEQ ID NO 2
<211> LENGTH: 21
<212> TYPE: DNA
<213> ORGANISM: Artificial sequence
<220> FEATURE:
<223> OTHER INFORMATION: primer

<400> SEQUENCE: 2
gcaaatggca ttctgacatc c                                               21
```